United States Patent [19]

Asano et al.

[11] 4,261,910
[45] Apr. 14, 1981

[54] PROCESS FOR THE PREPARATION OF CHLORAMBUCIL DERIVATIVES

[75] Inventors: Kiro Asano; Humio Tamura, both of Kukizaki; Hiromitsu Tanaka, Tokyo; Satoru Enomoto, Fujisawa, all of Japan

[73] Assignee: Kureha Kagaku Kogyo Kabushiki Kaisha, Tokyo, Japan

[21] Appl. No.: 62,789

[22] Filed: Aug. 1, 1979

[30] Foreign Application Priority Data

Aug. 14, 1978 [JP] Japan .................................. 53-98795
Dec. 8, 1978 [JP] Japan .................................. 53-152175

[51] Int. Cl.³ .......................... C07J 1/00; A61K 31/56
[52] U.S. Cl. ................................. 260/397.5; 424/238; 260/397.4
[58] Field of Search ................. 260/397.5, 397.4; /Steroids MS File

[56] References Cited

U.S. PATENT DOCUMENTS

| | | | |
|---|---|---|---|
| 3,963,707 | 6/1976 | Hogberg et al. | 424/243 |
| 4,029,778 | 6/1977 | Fex et al. | 424/243 |
| 4,150,126 | 4/1979 | Fex et al. | 424/243 |
| 4,180,504 | 12/1979 | Hansen et al. | 260/239.55 |
| 4,181,669 | 1/1980 | Hansen et al. | 260/397.44 |

Primary Examiner—Elbert L. Roberts
Attorney, Agent, or Firm—Oblon, Fisher, Spivak, McClelland & Maier

[57] ABSTRACT

The Chlorambucil derivatives are novel compounds having the formula (I).

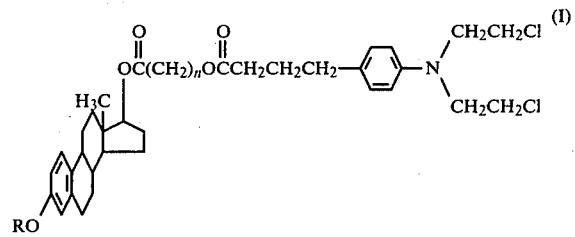

wherein R represents a hydrogen atom or an acyl group such as

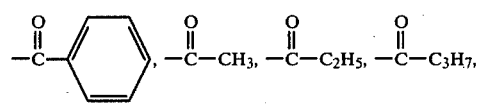

and n is 1 or 2.

The Chlorambucil derivatives can be produced by binding Chlorambucil to hydroxyl group at 17-position of estradiol or its derivative in the presence of a binding agent selected from the group consisting of compounds having the formula $X(CH_2)_nCOOH$ $X(CH_2)_nCOX$ $HOOC(CH_2)_nCOOH$ and $XOC(CH_2)_nCOX$ wherein n is 1 or 2 and X represents a halogen atom.

5 Claims, 1 Drawing Figure

PROCESS FOR THE PREPARATION OF CHLORAMBUCIL DERIVATIVES

BACKGROUND OF THE INVENTION

The present invention relates to novel antitumor drug 4-{p-[bis(2-chloroethyl)amino]phenyl}butyric acid (Chlorambucil) derivatives and a process for producing the same. More particularly, it relates to Chlorambucil derivatives obtained by chemically binding Chlorambucil to hydroxyl group at 17-position of estradiol or its derivative in the presence of a binding agent and antitumor drugs thereof.

As it is well-known, most of antitumor drugs affect to cancer cells and also normal cells and accordingly, they impart serious side effect. Thus, it is difficult to administrate for a long period so as to completely damage cancer cells.

The inventors have studied to overcome such disadvantages of the known antitumor drugs and to develop novel antitumor drugs having high therapeutic effect. As the result, the inventors have succeeded in obtaining novel antitumor estradiol derivatives, which selectively attach certain cancer cells and have low side effect.

SUMMARY OF THE INVENTION

It is an object of the present invention to provide novel Chlorambucil derivatives which selectively affect to cancer cells.

It is another object of the present invention to provide a process for producing novel Chlorambucil derivative.

It is the other object of the present invention to provide novel antitumor drugs of Chlorambucil derivatives.

The Chlorambucil derivatives of the present invention are novel compounds having the formula (I)

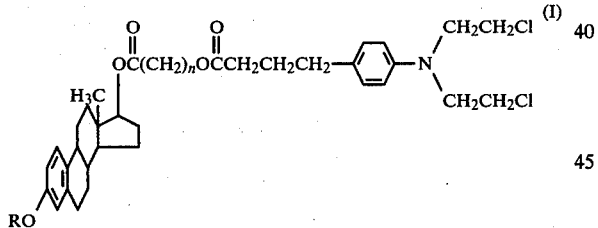

wherein R represents a hydrogen atom or an acyl group such as

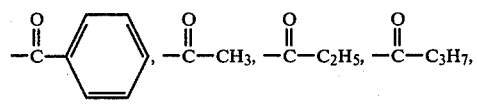

and n is 1 or 2.

The Chlorambucil derivatives of the present invention can be produced by binding Chlorambucil to hydroxyl group at 17-position of estradiol or its derivative in the presence of a binding agent selected from the group consisting of compounds having the formula

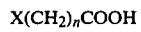

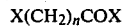

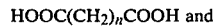

wherein n is 1 or 2 and X represents a halogen atom.

DETAILED DESCRIPTION OF THE PREFERRED EMBODIMENTS

Figure 1:
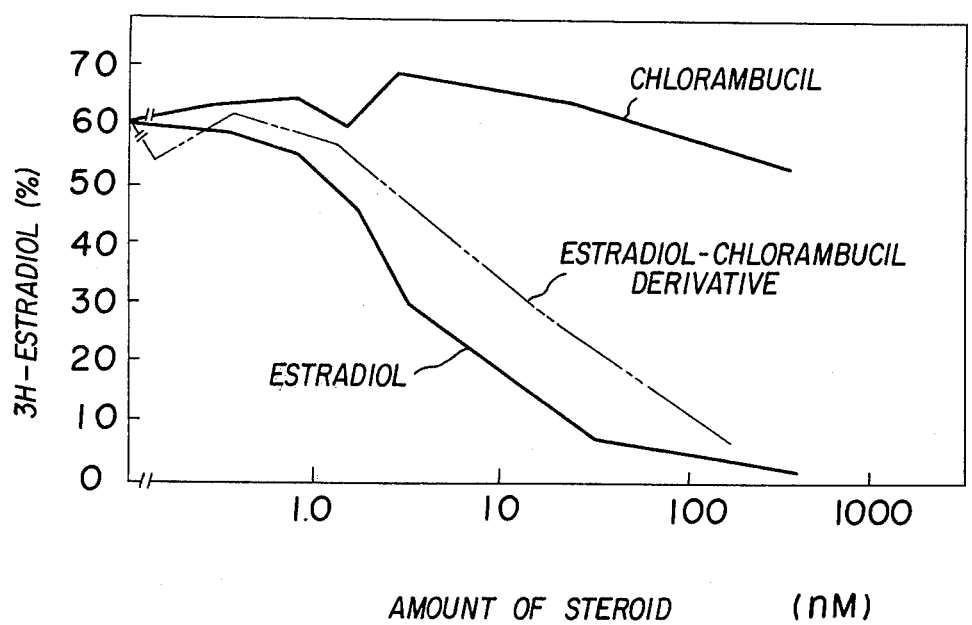

The Chlorambucil derivatives of the present invention are conjugates to Chlorambucil and estradiol or its derivative with a binding agent. The Chlorambucil derivatives of the present invention have special affinity to cancer cells and have special effect for selectively attacking cancer cells.

The specific cancer cells have receptors for the steroid hormones, especially estradiol derivatives as the component of the Chlorambucil derivatives of the present invention.

The receptors can be targets for the Chlorambucil derivatives of the present invention. Accordingly, the Chlorambucil derivatives of the present invention attack cancer cells having the receptor for estradiol and its derivatives.

The Chlorambucil derivatives of the present invention are selectively distributed to cancer cells of an organism to attack the cancer cells without a side effect.

The special feature of the present invention is to bond estradiol or its derivative of Chlorambucil without losing of active positions of estradiol or its derivative and without losing of antitumor active position of Chlorambucil.

It is preferable to convert OH group at 3-position of estradiol into an acyloxy group such as

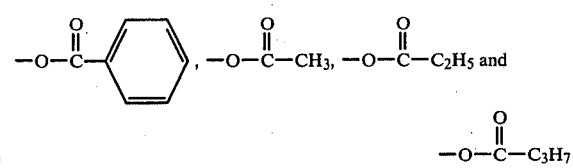

The acyloxy group is converted easily into OH group in an organism of a body to bond to the receptors in the cells.

The Chlorambucil derivatives of the present invention can be produced by binding Chlorambucil to hydroxyl group at 17-position of estradiol or its derivative in the presence of a binding agent.

The binding agent should not cause toxicity by binding them.

The optimum binding agents for binding estradiol or its derivative with Chlorambucil include monobromoacetylbromide, monochloroacetylchloride, monochloroacetic acid, monobromoacetic acid, etc.

The Chlorambucil and estradiol or its derivative can be bound with the binding agent by suitable processes.

For example, in one process, the binding agent firstly reacts with estradiol or an acylated estradiol and then the modified estradiol or its acylated derivative reacts with Chlorambucil. In the other process, the binding agent firstly reacts with Chlorambucil and then the modified Chlorambucil reacts with estradiol or an acylated estradiol.

In the former process, the binding agent reacts with nonactive position of estradiol or an acylated estradiol to obtain an ester having the formula

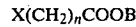

wherein B represents a moiety of estradiol or acylated estradiol removed the OH group at 17-position and X represents a halogen atom. Then, the halogen of the ester reacts with Chlorambucil to produce the Chlorambucil derivative of the present invention.

The reactions will be further illustrated.

The binding agent such as monobromoacetylbromide reacts with OH group at 17-position of estradiol or acylated estradiol having an acyl group at 3-position in a solvent such as carbon tetrachloride, chloroform, tetrahydrofuran, dimethylsulfoxide(DMSO), dimethylformamide(DMF), pyridine and acetone. The reaction product further reacts with Chlorambucil in a solvent such as dimethylsulfoxide, dimethylformamide, pyridine, toluene, carbon tetrachloride, chloroform, tetrahydrofuran (THF). Chlorambucil can be used in a form of an acid or its metal salt such as silver salt and an alkali salt.

The temperature of each reaction is usually ranging from −30° C. to 100° C. preferably from −10° C. to 80° C. The reaction time is usually ranging from 0.5 to 74 hours. The reaction product is purified by suitable purifying method to obtain the Chlorambucil derivatives of the present invention.

In the latter process, the binding agent reacts with carboxyl group of Chlorambucil to obtain a compound having the formula

ACOO(CH$_2$)$_n$COX wherein A represents a moiety of Chlorambucil removed the COOH group at 1-position. Then, the halogen (X) of the compound reacts with OH group at 17-position of estradiol or acylated estradiol having an acyl group at 3-position to produce the Chlorambucil derivatives of the present invention.

The solvents used in these reactions are respectively the same as those for the reaction of Chlorambucil or estradiol or the acylated estradiol.

The reaction temperature and the reaction time can be selected from the same ranges.

The OH group at 3-position of estradiol component in the Chlorambucil derivative of the present invention can be acylated before or after binding Chlorambucil to estradiol in the presence of the binding agent, though it is preferable to acylate estradiol before binding them.

The reactions for the acylated products will be further illustrated.

The OH group at 3-position of estradiol reacts with alkali metal hydroxide in a solvent such as THF to convert it to ONa group or OK group and then, the reaction product further react with an acylchloride such as benzoylchloride, acetylchloride and propionylchloride to obtain the acylated estradiol. Then, the binding agent such as monobromoacetylbromide reacts with OH group at 17-position of the acylated estradiol in a solvent such as DMSO, DMF, pyridine, acetone and THF. Then, the modified acylated estradiol reacts with Chlorambucil in a solvent such as DMSO, DMF, pyridine, toluene, carbon tetrachloride, chloroform and THF.

The temperature of each reaction is usually ranging from −30° C. to 100° C. preferably −10° C. to 80° C. The reaction time is usually ranging from 0.5 to 74 hours. The resulting product is purified by suitable purifying method to obtain the Chlorambucil derivatives of the present invention.

Certain processes for producing the Chlorambucil derivatives of the present invention will be described by certain examples which are illustration only and the conditions for the reactions can be selected as desired.

The Chlorambucil derivatives of the present invention have the formula (I) as the conjugates of Chlorambucil and estradiol or acylated estradiol. The fact was confirmed by IR spectrum, UV spectrum, NMR, TLC, Mass spectrum, Elemental analysis and melting point of the products.

According to the tests of acute toxicity, introduction of the compound into estrogen sensitive cells and antitumor effect, the Chlorambucil derivatives of the present invention have remarkably low toxicity, and remarkably high binding ability into estrogen sensitive cells and high antitumor effect.

The Chlorambucil derivatives of the present invention are especially effective for attacking cancer tissues and cells having estradiol. The chlorambucil derivatives of the present invention have not the specific sexual function of estradiol even though they are estradiol derivatives. The reason is not realized at the present stage. It is considered that such effects will be supported by certain unknown mechanism beside the medical effect based on the usual concept of the receptor.

When the Chlorambucil derivatives of the present invention are used as therapeutic medicine, medical compositions for administration can be prepared by the conventional methods for the known antitumor drugs.

The Chlorambucil derivatives of the present invention can be formulated in desirable forms for injection, oral administration, suppository or paste. When they are formulated in solid forms for oral administration such as tablet, pill, granules, powder, capsule, it is possible to admix a binder, a diluting agent, a filler, a lubricant, an oil, a surfactant or a disintegrator in the formulation. When they are formulated in liquid forms for oral administration, the formulation can be an aqueous suspension, an oily suspension, a solution, a syrup and a shake mixture. When they are formulated in a form of suppository, the formulation can be prepared by using a hydrophobic or hydrophilic base and a stabilizer, a disintegrator, or a coloring agent. When they are formulated in a form of injection, an aqueous solution, a solubilizer, a nutrient, a stabilizer, a surfactant can be added. In order to maintain or to improve medical effect, a base, an acid or a salt can be incorporated as desired. The amount of the active ingredient contained in the composition (preparation) is generally from 0.001% to 90% by weight and preferably from 0.01 to 60%.

The formulated Chlorambucil derivatives of the present invention can be administrated by oral administration, percutaneous adsorption, intramuscular injection, intraperitoneal injection, subcutaneous injection, intravenous injection, intrarectal injection and local administration.

The dose of the Chlorambucil derivative of the present invention is ranging from about 0.01 to 50 mg/kg/day/adult in the oral administration and it is ranging from about 0.001 to 20 mg/kg/day/adult in the intravenous injection.

The Chlorambucil derivatives of the present invention have the following characteristics.

(1) When cancer is formed in a tissue having its receptor, the product selectively attacks the cancer cells of the tissue to destroy the cancer cells. Thus, it is effective by only small dosage.

(2) The product has lower side effect is comparison with those of the administration of the Chlorambucil. Thus, it can be administrated for a long period and accordingly, cancer cells can be completely destroyed.

(3) The estradiol or acylated estradiol used as the carrier component in the Chlorambucil derivative, has a single structural composition and its physiologic activity is clearly known. Thus, the product can be administrated without any anxiety.

(4) The structure, and activity of the antitumor component in the Chlorambucil derivative are already known. Thus, the product can be administrated without any anxiety.

(5) The receptor of the cancer cells can be studied. The corresponding steroid hormone or its derivative can be selected as a carrier component for the Chlorambucil derivative. The therapeutic for various cancers can be considered by selecting the carrier component.

(6) The Chlorambucil derivative can be administrated by the conventional form of the formulation such as oral administration, injection and suppository. The Chlorambucil derivatives of the present invention can be also used as a stabilizer for high polymers especially polyolefins.

The present invention will be further illustrated by certain examples and references which are provided for purposes of illustration only and are not intended to be limiting the present invention.

EXAMPLE 1

Preparation of 3-hydroxy-1,3,5(10)-estratriene-17$\beta$-[4-{p-[bis(2-chloroethyl)amino]phenyl}butyryloxy]acetate (I) Preparation of 3-hydroxy-1,3,5(10)-estratriene-17$\beta$-monobromoacetate 10 Grams of 1,3,5(10)-estratriene-3,17$\beta$-diol was dissolved in 400 ml. of anhydrous tetrahydrofuran (THF), and then, 8.8 g. of pyridine was added.

A solution of 22.5 g. of monobromoacetylbromide in 74 g of carbon tetrachloride was added dropwise to the resulting solution at about $-5°$ C. to $-7°$ C. The mixture was kept for one night. After the reaction, the resulting precipitate was separated by a filtration. The solvent was distilled off from the filtrate. The residue was dissolved in ether and recrystallized from ether to obtain 1,3,5(10)-estratriene-3,17$\beta$-bis(monobromoacetate). 2 Grams of the product was dissolved in 900 ml of methanol and the solution was cooled to $-5°$ C. A solution of 0.24 g. of $K_2CO_3$ in 20 ml. of water was added dropwise to the resulting solution. After the reaction for 30 minutes, 1000 ml. of water was added and the resulting precipitate was separated and dried. It was confirmed that the product was 3-hydroxyl,-1,3,5(10)-estradiene-17$\beta$-monobromoacetate by the elementary analysis and the IR spectrum.

(II) Preparation of 3-hydroxy-1,3,5(10)-estratriene-17$\beta$-[4{p-[bis(2-chloroethyl)amino]phenyl}butyryloxy]acetate. (Chlorambucil-estradiol conjugate)

200 Milligrams of silver [4-{p-[bis(2-chloroethyl)amino]phenyl}butyrate](silver salt of Chlorambucil) was added in 10 ml of DMSO to form a white colloidal solution. Then, 190.8 mg. of 3-hydroxy-1,3,5(10)-estratriene-17$\beta$-monobromoacetate was added and the mixture was stirred at room temperature for 64 hours in the dark. The precipitate was changed to yellowish green color. A small amount of acetone was added and the precipitate was separated by a filtration through G-4 filter. The precipitate was changed from yellowish green color to blackkish green color by the irradiation of light. The filtrate was colorless and transparent. DMSO was distilled off under a reduced pressure on a water bath at 80° C. and 100 ml. of water was added to precipitate white crystals. The crystals were kept for 1 hour to remove DMSO and the crystals were separated through G-4 filter and thoroughly washed with a distilled water and dried under a reduced pressure in a desiccator. A crude yield was 330.5 mg.

a. Purification of the Product 330.5 Milligrams of crude crystals were dissolved in a mixed solvent of 50 vol. parts of cyclohexane and 10 vol. parts of ethyl acetate. The solution was slowly passed through a column filling 40 g of silica gel and the product was gradually separated to obtain 188.2 mg (yield: 62.86%) of pure product.

The results of elementary analysis, melting point and IR spectrum of the product are as follows.

Elementary analysis:

|  | C | H | N | Cl |
|---|---|---|---|---|
| Found (%) | 66.0 | 7.0 | 2.3 | 11.0 |
| Calculated (%) | 66.22 | 6.98 | 2.27 | 11.52 |

Melting point: Semimelt at 25° C.

IR spectrum (cm$^{-1}$) 3420, 2920, 2840, 1750, 1740, 1612, 1582, 1516, 1450, 1380, 1350, 1280, 1250, 1210, 1175, 1142, 1070, 1000, 960, 917, 867, 810, 800, 740, 655

EXAMPLE 2

Preparation of 3-benzoyloxy-1,3,5(10)-estratriene-17$\beta$-[4-{p-[bis(2-chloroethyl)amino]phenyl}butyryloxy]acetate 10 Grams of 1,3,5(10)-estratriene-3,17$\beta$-diol was dissolved in 100 ml. of THF and 10 ml of an aqueous solution containing 1.47 g. of NaOH was added. The mixture was stirred at room temperature for 30 minutes. Then, the reaction mixture was concentrated dried under a reduced pressure on a water bath at 80° C. to remove water. The residue was dissolved in anhydrous THF and 50 ml. of ethyl ether solution containing 5.5 g. of benzoylchloride was added dropwise to the resulting solution and the reaction was carried out at room temperature for 16 hours. After the reaction, the resulting sodium chloride was separated by the conventional method. The filtrate was evaporated to dryness under a reduced pressure. In order to removed the unreacted benzoylchloride, 200 ml. of 0.1 N-NaOH aqueous solution was added and the mixture was stirred at room temperature for 15 minutes. The resulting white crystals were separated through G-3 filter and thoroughly washed with distilled water and dried under a reduced pressure in a desiccator.

The product was analyzed by a thin layer chromatography on a silica gel with a mixed developing solvent (ethyl acetate and cyclohexane at a ratio of 50:30 by volume) to give the main spot of Rf: 0.34.

The crude crystals were recrystallized from ethyl acetate and then obtained 8.6 g. of white crystals.

It was confirmed that the product is 17β-hydroxy-1,3,5(10)-estratriene-3-benzoate by means of the melting point, the elementary analysis and the IR spectrum.

In THF, 7.0 g. of the resulting product was dissolved and 2.0 g. of pyridine was added and the mixture was cooled to −5° C.

A solution containing 15.5 g. of 30% monobromoacetylbromidecarbon tetrachloride in 50 ml of THF was gradually added dropwise to the resulting mixture. After the addition, the mixture was stirred at −5° C. for 2 hours and then, on an ice bath for 4 hours and was kept in a refrigerator for 16 hours. After the reaction, the resulting white precipitate was separated through G-4 filter and dried under a reduced pressure on a water bath at 30° C. and 200 ml. of ethyl ether was added and the mixture was stirred to obtain 5.3 g of white crystals.

The results of the elementary analysis and the melting point are as follows.

Elementary analysis:

|  | C | H | Br |
|---|---|---|---|
| Found (%) | 64.3 | 5.8 | 15.7 |
| Calculated (%) | 64.23 | 5.78 | 15.8 |

Melting point: 145°–146° C.

The product was analyzed by a thin layer chromatography on a silica gel with a mixed developing solvent (ethyl acetate and cyclohexane at a ratio of 50:30 by volume) to give the single spot of Rf: 0.77.

In the IR spectrum, the absorption based on OH group was not found and accordingly, it was confirmed that the product is 3-benzoyloxy-1,3,5(10)-estratriene-17β-monobromoacetate.

IR spectrum: (cm$^{-1}$) 2920, 1735, 1728, 1595, 1579, 1490, 1448, 1412, 1382, 1286, 1280, 1260, 1210, 1200, 1170, 1145, 1095, 1075, 1019, 1004, 897, 780, 700, 680.

182.3 Milligrams of 3-benzoyloxy-1,3,5(10)-estratriene-17β-monobromoacetate and 148.5 mg. 0.6 silver 4-{p-[bis(2-chloroethyl)amino]phenyl}butyrate were added in 5 ml. of DMSO and the reaction was carried out at room temperature for 3 days in the dark. After the reaction, the precipitate of silver bromide was separated by a filtration and 400 ml. of water was added to the filtrate. The resulting white precipitate was separated by a centrifugal separation. The precipitate was dissolved in 50 ml. of acetone and the insoluble material was separated by a filtration through G-4 filter.

The filtrate was evaporated to dryness under a reduced pressure to obtain 165 mg. of an oily product.

The product was analyzed by a thin layer chromatography on a silica gel with a mixed developing solvent (ethyl acetate and cyclohexane at a ratio of 10:50 by volume) to give a main spot of Rf: 0.44.

Since the unreacted material was remained, the reaction product was chromatographed on a silica gel with a mixed solvent (ethyl acetate and cyclohexane at a ratio of 10:50 by volume) to obtain a purified product. The purified product was a white crystal compound at 20° C. The results of the elementary analysis and IR spectrum of the product are as follows. It was confirmed that the product is 3-benzoyloxy-1,3,5(10)-estratriene-17β-[4-{p-[bis(2-chloroethyl)amino]phenyl}-butyryloxy]acetate.

Elementary analysis:

|  | C | H | N | Cl |
|---|---|---|---|---|
| Found (%) | 68.5 | 6.60 | 1.99 | 9.79 |
| Calculated (%) | 68.33 | 6.53 | 1.94 | 9.86 |

Melting point (°C.) 110–111

IR spectrum: (cm$^{-1}$) 2920, 2860, 1755, 1735, 1612, 1582, 1516, 1491, 1450, 1420, 1380, 1355, 1260, 1224, 1210, 1174, 1145, 1079, 1022, 1005, 960, 915, 890, 800, 740, 705.

EXAMPLE 3

Preparation of 3-propionyloxy-1,3,5(10)-estratriene-17β-[4{p-[bis(2-chloroethyl)amino]phenyl}butyryloxy]acetate.

10 Grams of 1,3,5(10)-estratriene-3,17β-diol was dissolved in 100 ml. of THF and 10 ml of an aqueous solution containing 1.47 g of NaOH in 10 ml. of water was added and the mixture was stirred at room temperature for 30 minutes. The reaction product was concentrated to dryness under a reduced pressure on a water bath at 80° C. to remove water. The residue was dissolved in anhydrous THF and a solution containing 3.40 g. of propionyl chloride in 50 ml of anhydrous THF was added dropwise and the reaction was carried out at room temperature for 16 hours. After the reaction, the precipitate of sodium chloride was separated and the filtrate was evaporated to dryness under a reduced pressure and the residue was recrystallized from ethanol to obtain 9 g. of white crystals.

It was confirmed that the product is 17β-hydroxy-1,3,5(10)-estratriene-3-propionate according to the elementary analysis and the IR spectrum.

7.0 Grams of the product was dissolved in 70 ml. of anhydrous THF and 3.0 g. of pyridine was added and the mixture was cooled to −5° C. A solution containing 17.3 g. of 30% monobromoacetylbromide-carbon tetrachloride in 50 ml. of THF was added dropwise to the resulting mixture. After the addition, the mixture was kept at −5° C. for 2 hours and then in a refrigerator for 16 hours to react them. After the reaction, the resulting precipitate was separated by a filtration. The filtrate was evaporated to dryness under a reduced pressure on a water bath at 30° C., and then, 200 ml. of ethyl ether was added and the mixture was stirred to obtain 6.0 g. of white crystals. The filtrate was further concentrated to obtain 3.5 g. of white crystals. The crystals were recrystallized from a mixed solvent of ether and ethanol.

The result of the elementary analysis is as follows.

Elementary analysis:

|  | C | H | Br |
|---|---|---|---|
| Found (%) | 61.5 | 6.5 | 17.9 |
| Calculated (%) | 61.43 | 6.45 | 17.78 |

In the IR spectrum, the absorption based on OH group was not found and accordingly, it was confirmed that the product is 3-propionyloxy-1,3,5(10)-estratriene-17β-monobromoacetate.

1.0 Grams of the product and 0.91 g of silver 4-{p-[bis(2-chloroethyl)amino]phenyl}butyrate were dispersed and dissolved in 50 mg of DMSO and the reaction was carried out at room temperature for 3 days in the dark. After the reaction, the precipitate of silver bromide was separated by a filtration and 4 liters of water was added. The precipitate was separated by a centrifugal separation and the white precipitate was dissolved in 50 ml. of acetone and the insoluble material was separated by a filtration through G-4 filter. The filtrate was evaporated to dryness under a reduced pressure to obtain 1.3 g of an oily product.

The product was chromatographed on a silica gel with a mixed solvent of ethyl acetate and cyclohexane at a ratio of 10:50 by volume to purify it. The purified product was a viscous oily product at 20° C.

The results of the elementary analysis and the IR spectrum are as follows.

Elementary analysis:

|  | C | H | N | Cl |
|---|---|---|---|---|
| Found (%) | 67.1 | 7.0 | 2.1 | 11.0 |
| Calculated (%) | 66.0 | 6.99 | 2.08 | 10.56 |

IR spectrum: (cm$^{-1}$) 2916, 2840, 1750, 1740, 1610, 1512, 1488, 1441, 1415, 1379, 1361, 1270, 1210, 1200, 1170, 1140, 1068, 1004, 956, 931, 885, 817, 793, 735 cm$^{-1}$ It was confirmed that the product is 3-propionyloxy-1,3,5(10)-estratriene-17β-[4-{p-[bis (2-chloroethyl)amino]phenyl}butyryloxy]acetate.

EXAMPLE 4

Preparation of
3-acetoxy-1,3,5(10)-estratriene-17β-[4-{p-[bis(2-chloroethyl)amino]phenyl}butyryloxy]acetate 1.0 Gram of 3-acetoxy-1,3,5(10)-estratriene-17β-monobromoacetate obtained by the same process of Example 2, and 0.9 g of silver 4-{p-[bis(2-chloroethyl)amino]phenyl}butyrate were added in 50 ml of DMSO and the reaction was carried out at 25° C. for 3 days in the dark. After the reaction, the precipitate of silver bromide was separated and 4 liter of water was added to the filtrate. The resulting white precipitate was separated by a centrifugal separation. The precipitate was dissolved in 50 ml. of acetone. The insoluble material was separated through G-4 filter and the filtrate was evaporated to dryness under a reduced pressure to obtain 1.2 g. of an oily product. The product was chromatographed on a silica gel with a mixed solvent of ethyl acetate and cyclohexane at a ratio of 10:50 by volume. The purified product was a viscous oily material at 20° C.

The result of the elementary analysis is as follows.
Elementary analysis:

|  | C | H | N | Cl |
|---|---|---|---|---|
| Found (%) | 66.0 | 6.9 | 2.0 | 10.9 |
| Calculated (%) | 65.64 | 6.84 | 2.13 | 10.79 |

In the IR spectrum, the absorption based on OH group was not found and accordingly, it was confirmed that the product is 3-acetoxy-1,3,5(10)-estratriene-17β-[4-{p-[bis(p-chloroethyl)amino]phenyl}butyryloxy]acetate.

IR spectrum: (cm$^{-1}$) 2915, 2840, 1750, 1740, 1610, 1512, 1488, 1442, 1415, 1378, 1360, 1270, 1210, 1200, 1170, 1140, 1068, 1005, 956, 931, 885, 817, 793, 735

EXAMPLE 5

1 Gram of 3-acetoxy-1,3,5(10)-estratriene-17β-monobromoacetate and 0.8 g. of sodium 4-{p-[bis(2-chloroethyl)amino]phenyl}butyrate were added to 50 ml. of THF to react them at 60° C. for 24 hours.

After the reaction, the precipitate was separated by the filtration and the filtrate was concentrated and dried. The product was separated and purified by a silica gel column with a mixed solvents of ethyl acetate and cyclohexane to obtain 0.9 g. of the purified product. The product was 3-acetoxy-1,3,5-(10)-estratriene-17β-{4-{p-[bis(2-chloroethyl)amino]phenyl}butyryloxy}acetate.

EXAMPLE 6

Preparation of
3-acetoxy-1,3,5(10)-estratriene-17β-[4-{p-[bis(2-chloroethyl)amino]phenyl}butyryloxy]acetate 200 Milligrams of silver 4-{p-[bis(2-chloroethyl)amino]phenyl}butyrate (silver salt of Chlorambucil) was added in 10 ml of DMSO to form a white colloidal solution. Then, 190.8 mg. of 3-hydroxy-1,3,5(10)-estratriene-17β-monobromoacetate was added to the colloidal solution and the mixture was stirred at room temperature for 64 hours in the dark. After 64 hours, the precipitate was varied to yellowish green color. A small amount of acetone was added to the precipitate and the precipitate was separated by a filtration through G-4 filter. The filtrate was colorless and transparent DMSO was distilled off on a water bath at 80° C. and then, 100 ml of water was added to precipitate white crystals. The mixture was kept for 1 hour and then, DMSO was distilled off. The white crystals were separated by a filtration through G-4 filter and then, washed with distilled water and dried under a reduced pressure in a desiccator. A crude yield was 330.5 mg..

330.5 Milligrams of the crude product was dissolved in a mixed solvent of cyclohexane and ethyl acetate at a ratio of 50:10 by volume. The solution was slowly passed through a column filling 40 g of silica gel to gradually separate the product and 188.2 mg. (yield 62.86%) of a pure product was obtained.

The results of the elementary analysis and the melting point of the product are as follows.
Elementary analysis:

|  | C | H | N | Cl |
|---|---|---|---|---|
| Found (%) | 66.0 | 7.0 | 2.3 | 11.0 |
| Calculated (%) | 66.22 | 6.98 | 2.27 | 11.52 |

Melting point: Semimelt at 25° C.

It was confirmed that the product is 3-hydroxy-1,3,5(10)-estratriene-17β-[4-{p-[bis(2-chloroethyl)amino]phenyl}butyryloxy]acetate.

50 Milligrams of the product was dissolved in 1 ml. of anhydrous pyridine and 1 ml. of acetic anhydride was added to react them in a refrigerator for 16 hours. After the reaction, the reaction mixture was concentrated and dried under a reduced pressure on a water bath at 30° C. The residue was admixed with distilled water and the mixture was kept for 1 hour to precipitate an oily product in white colloidal foam. Pyridine and acetic acid were removed with distilled water and the product was washed with water to be neutral. The oily product was separated from an aqueous solution and concentrated and dried in a desiccator under a reduced pressure to obtain 45 mg. of an oily product.

The product was analyzed by a thin layer chromatography on a silica gel with a mixed developer solvent of ethyl acetate and cyclohexane at a ratio of 30:50 by volume to give a single spot of Rf: 0.78.

The product was chromatographed on a silica gel with a mixed solvent of ethyl acetate and cyclohexane at a ratio of 10:50 by volume to purify the product. The purified product was a viscous oily compound at 20° C.

The result of the elementary analysis is as follows.
Elementary analysis

|  | C | H | N | Cl |
|---|---|---|---|---|
| Found (%) | 66.0 | 6.5 | 2.0 | 10.9 |
| Calculated (%) | 65.64 | 6.84 | 2.13 | 10.79 |

In the IR spectrum, the absorption based on OH group was not found and accordingly, it was confirmed that the product is 3-acetoxy-1,3,5(10)-estratriene-17$\beta$-[4-{p-[bis(2-chloroethyl)amino]phenyl}butyryloxy]acetate.

IR spectrum: (cm$^{-1}$) 2915, 2840, 1750, 1740, 1610, 1512, 1488, 1442, 1415, 1378, 1360, 1270, 1210, 1200, 1170, 1140, 1068, 1005, 956, 931, 885, 817, 793, 735.

EXAMPLE 7

Preparation of
3-propionyloxy-1,3,5(10)-estratriene-17$\beta$-[4-{p-[bis(2-chloroethyl)amino]phenyl}butyryloxy]acetate 50 Milligrams of 3-hydroxy-1,3,5(10)-estratriene-17$\beta$-[4-{p-[bis(2-chloroethyl)amino]phenyl}butyryloxy]acetate was dissolved in 1 ml. of anhydrous pyridine and 1.5 ml. of propionic anhydride was added and the mixture was kept in a refrigerator for one day. The reaction mixture was evaporated to dryness under a reduced pressure on a water bath at 30° C. The residue was admixed with distilled water and the mixture was kept for 2 hours to form a colloidal oily product. Pyridine and acetic acid were removed with distilled water and the product was washed with water to be neutral. Water phase was separated and the oil phase was dried under a reduced pressure in a desiccator to obtain 40 mg. of an oily product. The product was chromatographed on a silica gel with a mixed solvent of ethyl acetate and cyclohexane at a ratio of 10:50 by volume to purify it. The purified product was a viscous oily compound. In the IR spectrum, the absorption at 3600–3200 cm$^{-1}$ was not found. In view of the result, it was confirmed that the product is 3-propionyloxy-1,3,5(10)-estratriene-17$\beta$-[4-{p-[bis(2-chloroethyl)amino]-phenyl}butyryloxy]acetate.

EXAMPLE 8

Preparation of
3-benzoyloxy-1,3,5(10)-estratriene-17$\beta$-[4-{p-[bis(2-chloroethyl)amino]phenyl}butyryloxy]acetate 50 Milligrams of 3-hydroxy-1,3,5(10)-estratriene-17$\beta$-[4-{p-[bis(2-chloroethyl)amino]phenyl}butyryloxy]acetate was dissolved in 1 ml. of anhydrous pyridine and 2 g. of benzoic anhydride was added and the mixture was kept in a refrigerator for one day. The reaction mixture was evaporated to dryness under a reduced pressure on a water bath at 30° C. The residue was admixed with distilled water and the mixture was kept for 1.5 hours to form a colloidal oily product. Pyridine and acetic acid were removed with distilled water and the product was washed with water to be neutral. The water phase was separated and the oil phase was evaporated to dryness under a reduced pressure in a desiccator to obtain 45 mg. of an oily product.

The product was chromatographed on a silica gel with a mixed solvent of ethyl acetate and cyclohexane at a ratio of 10:50 by volume to purify the product. The purified product was a viscous oily compound.

In the IR spectrum, the absorption band at 3600 to 3200 cm$^{-1}$ was not found. In view of the fact, it was confirmed that the product is 3-benzoyloxy-1,3,5(10)-estratriene-17$\beta$-[4-{p-[bis(2-chloroethyl)amino]-phenyl}butyryloxy]acetate.

TEST 1

Acute toxicities and antitumor activities (in vivo) of the Chlorambucil derivatives of the present invention (1) Acute toxicity (LD$_{50}$)

In the measurement of LD$_{50}$, eight ICR-JCL female mice (5 week age) were used as one group to breed in a transparent polycage, and each drug was dissolved in olive oil and administrated by routes of intraperitoneal injection (i.p.), oral administration (p.o.) and subcutaneous injection (s.c.), to the mice at one dose, and then, their value of LD$_{50}$ by Litchfield-Wilcoxon graph method is obtained after 7 days. The results are as follows. LD$_{50}$ of Chlorambucil was i.p. 20 mg./kg., p.o. 80 mg./kg., and s.c. 26 mg./kg., LD$_{50}$ of the sample No. 2 in Table 1 of the present invention was i.p. greater than 3000 mg./kg., p.o. greater than 6000 mg./kg. and s.c. greater than 3000 mg./kg..

(2) Antitumor Test (in vivo)

Pieces of human breast cancer cells having steroid hormone receptor were subcutaneously implanted under the arm of mice (BALB/C-nu/nu) (5 week age) to form solid tumors. After the solid tumors were established, each dispersion or solution of the active ingredient in olive oil was administrated by oral dose or intraperitoneal injection each other day for 10 times or every days for 20 times. Twenty five days from the initial administration, the tumors were excised. Efficiency of inhibition of tumor proliferation was measured from (A) each average weight of excised tumors for 10 mice (the active ingredient was administrated) and (B) each average weight of excised tumors for 10 control mice.

$$\text{Inhibitory effect of tumor (\%)} = \left(1 - \frac{A}{B}\right) \times 100$$

In both of the subcutaneously an orally administration of Chlorambucil at a dose of 15 mg./kg., the efficiency of inhibition was in about 50 to 70% whereas in the administrations of the Chlorambucil derivatives of the present invention, the efficiencies of inhibition were more than 90%. When the Chlorambucil derivatives of the present invention were administrated, all of the mice were survived.

In the observation in autopsy serious changes of spleen, uterus and thymus were found after the administration of Chlorambucil, whereas no change was found after the administration of the sample of the present invention.

TABLE 1

| | LD$_{50}$ | | | |
|---|---|---|---|---|
| Sample No. | 1 | 2 | 3 | 4 |
| LD$_{50}$ (mg/kg) | | 80 | 6000< | 3000< | 3000< |

TABLE 1-continued

| Sample No. | LD50 | | | |
|---|---|---|---|---|
| | 1 | 2 | 3 | 4 |
| (Oral administration) LD50 (mg/kg) (Subcutaneous administration) | 26 | 2000< | 2000< | 2000< |

TABLE 2

| | Antitumor effect | | | | | | | | |
|---|---|---|---|---|---|---|---|---|---|
| Sample No. | 1 | | 2 | | 3 | | 4 | | 5 |
| Antitumor test | | | | | | | | | |
| Oral administration | | | | | | | | | |
| Dose (mg/kg) | 10 | 15 | 10 | 15 | 10 | 15 | 10 | 15 | 15 |
| Survived ratio * | 8/10 | 7/10 | 10/10 | 10/10 | 10/10 | 10/10 | 10/10 | 10/10 | 10/10 |
| Efficiency of inhibition (%) | 55 | 70 | 92 | 98 | 91 | 93 | 93 | 97 | 0 |
| Subcutaneous administration | | | | | | | | | |
| Dose (mg/kg) | 5 | 10 | 5 | 10 | 5 | 10 | 5 | 10 | 10 |
| Survived ratio * | 9/10 | 7/10 | 10/10 | 10/10 | 10/10 | 10/10 | 10/10 | 10/10 | 10/10 |
| Efficiency of inhibition (%) | 53 | 71 | 90 | 98 | 93 | 95 | 92 | 94 | 0 | note:
Sample No. 1.: Chlorambucil
Sample No. 2.: 3-benzoyloxy-1,3,5(10)-estratriene-17β-[4-{p-[bis(2-chloroethyl)amino]phenyl}butyryloxy]acetate
Sample No. 3.: 3-acetoxy-1,3,5(10)-estratriene-17β-[4-{p-[bis(2-chloroethyl)amino]phenyl}butyryloxy]acetate
Sample No. 4.: 3-propionyloxy-1,3,5(10)-estratriene-17β-[4-{p-[bis(2-chloroethyl)amino]phenyl}butyryloxy]acetate
Sample No. 5.: Olive oil (control)

TEST 2

In accordance with the test I, except administrating each active ingredient in a form of dispersion dispersed in Polysolvate 80 (emulsifier) by an intraperitoneal injection in the test of antitumor effect. The result is as follows.

| | Chlorambucil | 3-hydroxy-1,3,5-(10)-estratriene-17 β-[4-{p-[bis(2-chloroethyl)amino]phenyl} butyryloxy]acetate | |
|---|---|---|---|
| Dose (mg./kg.) | 5 | 0.5 | 5 |
| Inhibitory effect (%) | 30 | 91 | 97 |
| Acute toxicity test LD50 | 20 | 1000< | |

TEST 3

Binding function of 3-hydroxy-1,3,5(10)-estratriene-17β-[4-{p-[bis(2-chloroethyl)amino]phenyl}-butyryloxy]acetate to estrogen sensitive cells.

Estradiol labelled by tritium ($^3$H) was incubated with uterus of rabbit to bind it and then, the sample was added to the system to measure the amount of free $^3$H-estradiol which was replaced by the added estradiol. The results are shown in FIG. 1. It was found that free $^3$H-estradiol was increased as the same with estradiol itself. The fact shows that the sample has the binding function to estrogen receptor.

COMPOSITION

Formula 1

| Active ingredient obtained by Example 3 | 50 wt. parts |
|---|---|
| Mannitol | 35 wt. parts |
| Sorbitol | 25 wt. parts |
| Carboxymethyl cellulose | 5 wt. parts |
| Magnesium stearate | 5 wt. parts |
| Talc | 40 wt. parts |

The components were mixed and pulverized and compressed to form a tablet having a diameter of 10 mm.

Formula 2

| Active ingredient obtained by Example 2 | 100 wt. parts |
|---|---|
| Lactose | 500 wt. parts |
| Sugar fatty acid ester | 10 wt. parts |
| Starch | 100 wt. parts |
| Water (1% sodium carboxy-methyl cellulose) | 100 wt. parts |

The components were kneaded and extruded through a pelleter in a form of granule and then, dried and sieved to remain the particles ranging from 10 to 24 mesh to prepare granules for oral administration.

Formula 3

The granules of Formula 2 were filled in a commercially available capsule to prepare 0.5 cc capsule.

Formula 4

| Active ingredient obtained by Example 1 | 5 wt. parts |
|---|---|
| Olive oil | 95 wt. parts |

The components were heated and mixed and sterilized to prepare an injection.

What is claimed is:

1. A process for producing Chlorambucil derivative having the formula (I) which comprises reacting Chlorambucil and hydroxyl group at 17-position of estradiol or acylated estradiol in the presence of a binding agent selected from the group consisting of compounds having the formula

$X(CH_2)_nCOOH$

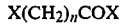

$X(CH_2)_nCOX$

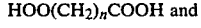

$HOO(CH_2)_nCOOH$ and

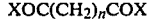

$XOC(CH_2)_nCOX$ wherein n is 1 or 2 and X is a halogen atom.

2. A process according to claim 1 wherein said binding agent firstly reacts with hydroxyl group at 17-position of estradiol or acylated estradiol in a solvent and then, the modified estradiol or acylated estradiol reacts with carboxyl group of Chlorambucil in a solvent.

3. A process according to claim 1 wherein said binding agent firstly reacts with carboxyl group of Chlorambucil in a solvent and then, the modified Chlorambucil reacts with hydroxyl group at 17-position of estradiol or acylated estradiol in a solvent.

4. A process according to claim 1 wherein Chlorambucil derivative having the formula (I) wherein R is hydroxyl group is acylated with an acid anhydride or an acid halide in a solvent.

5. A process according to claim 1 wherein Chlorambucil is converted into silver salt, alkali salt of Chlorambucil and then, it reacts with the binding agent or the modified estradiol or acylated estradiol in a solvent.

* * * * *